United States Patent

Hauck et al.

[11] 3,971,823
[45] July 27, 1976

[54] CYCLITOLAMINES

[75] Inventors: Frederic P. Hauck, Somerville, N.J.;
Joseph E. Sundeen, Yardley, Pa.;
Joyce Reid, Highland Park, N.J.

[73] Assignee: E. R. Squibb & Sons, Inc., Princeton, N.J.

[22] Filed: Dec. 2, 1975

[21] Appl. No.: 636,891

[52] U.S. Cl. .............................. 260/490; 260/559 B; 260/570.7; 424/199; 424/311
[51] Int. Cl.² .................... C07C 93/00; C07C 93/12
[58] Field of Search ..................... 260/490, 570.7 R

[56] References Cited
UNITED STATES PATENTS

| | | | |
|---|---|---|---|
| 3,159,634 | 12/1964 | Jack et al. | 260/570.7 |
| 3,894,031 | 7/1975 | Hauck et al. | 260/490 |

OTHER PUBLICATIONS
Chem. Abstracts, 52:7311g (1958).

*Primary Examiner*—Vivian Garner
*Attorney, Agent, or Firm*—Lawrence S. Levinson; Merle J. Smith; Donald J. Barrack

[57] ABSTRACT

Compounds having the structure

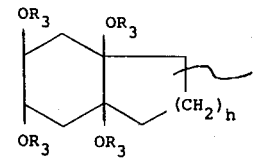

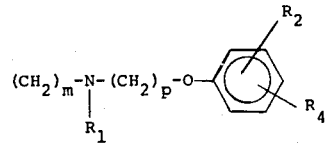

wherein $R_1$ is alkyl or arylalkyl; $R_2$ is hydrogen, halogen, alkyl, or alkoxy; $R_3$ is alkanoyl; $R_4$ is hydrogen or alkanoyl; $n$ is 1, 2 or 3; $m$ is 1, 2, 3 or 4; and $p$ is 2, 3 or 4; are useful for the treatment of hypertension.

17 Claims, No Drawings

CYCLITOLAMINES

SUMMARY OF THE INVENTION

Compounds having the formula

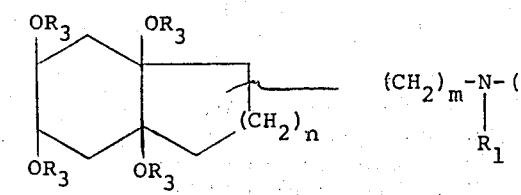

and the pharmaceutically acceptable acid-addition salts thereof, are useful for the treatment of hypertension. In formula I, and throughout the specification, the symbols are as defined below.

$R_1$ is alkyl or arylalkyl;
$R_2$ is hydrogen, halogen, alkyl, or alkoxy;
$R_3$ is alkanoyl;
$R_4$ is hydrogen or alkanoyl;
$n$ is 1, 2 or 3;
$m$ is 1, 2, 3 or 4; and
$p$ is 2, 3 or 4;
with the proviso that when $R_4$ is alkanoyl, $R_3$ and $R_4$ are the same.

The term "alkyl", as used throughout the specification, refers to straight or branched chain saturated hydrocarbon groups having 1 to 6 carbon atoms.

The term "alkoxy", as used throughout the specification, refers to groups having the formula Y-O- wherein Y is alkyl as defined above.

The term "alkanoyl", as used throughout the specification, refers to groups having the formula $$Y-\overset{O}{\underset{\|}{C}}-$$

wherein Y is alkyl as defined above.

The term "aryl", as used throughout the specification, refers to phenyl, or phenyl substituted with one or two halogen, alkyl or alkoxy groups. Phenyl is the preferred aryl group.

DETAILED DESCRIPTION OF THE INVENTION

The products of formula I can be prepared from compounds having the structure

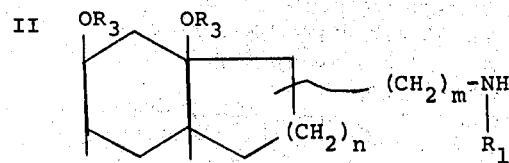

or

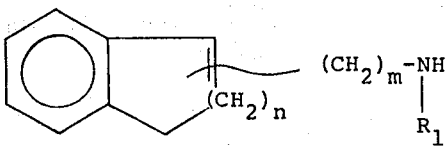

The compounds of formulas II and III are known; see, for example, U.S. Pat. No. 3,894,031 issued July 8, 1975.

Those compounds of formula I wherein $R_4$ is hydrogen can be prepared by the reaction of a compound of formula II with a compound having the structure

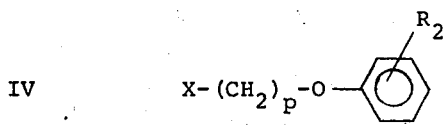

wherein X is chlorine or bromine. The reaction can be run in an organic solvent, e.g., benzene, in the presence of an organic base, e.g., triethylamine. Reaction conditions are not critical, but the reaction will most preferably be run at the reflux temperature of the solvent.

Those compounds of formula I wherein $R_4$ is alkanoyl can be prepared by first subjecting a compound of formula III to a Birch reduction to yield a compound having the structure

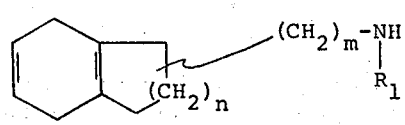

A diene of formula V can be reacted with a compound of formula IV to yield a compound having the structure

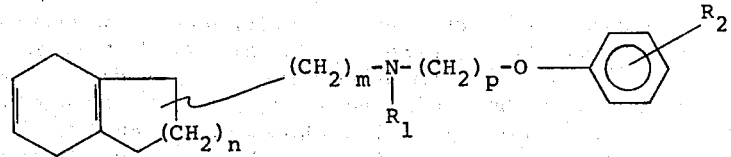

The reaction can be run in an organic solvent, e.g., toluene, benzene, etc. Reaction conditions are not critical, but the reaction will preferably be run at the reflux temperature of the solvent.

Alternatively, a compound of formula VI can be prepared by reacting a diene of formula V with a compound having the structure

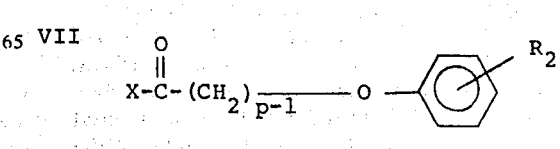

wherein X is chlorine or bromine, to yield a compound having the structure

VIII

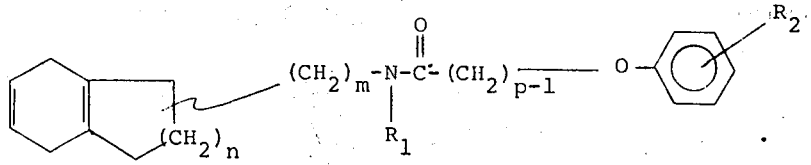

The reaction can be run in an acid accepting solvent, e.g., pyridine. Reaction conditions are not critical, but the reaction will preferably be run at, or below, room temperature. The diene amide of formula VIII can be reduced, e.g., with a mixed metal hydride such as lithium aluminum hydride, to give a diene of formula VI.

Treatment of phenoxyalkyl diene of formula VI with formic acid and hydrogen peroxide, followed by basic hydrolysis, yields a tetrol derivative having the structure

IX

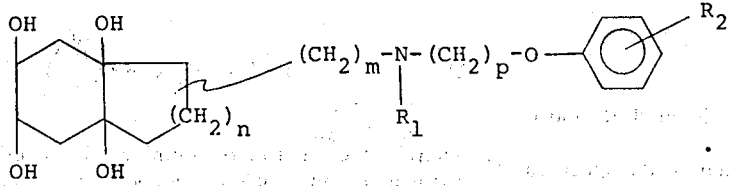

The tetrols of formula IX are novel intermediates, and as such, they constitute a part of this invention. A tetrol derivative of formula IX can be converted to the corresponding compound of formula I, wherein $R_4$ is alkanoyl, by reacting with an acid anhydride having the structure

X            $(R_3)_2O$, in the presence of perchloric acid.

The compounds of formula I can be converted to their pharmaceutically acceptable acid-addition salts using methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

The compounds of formula I, and the pharmaceutically acceptable acid-addition salts thereof, inhibit the conversion of Angiotensin I to Angiotensin II. They are useful as hypotensive agents in mammals, e.g., domestic animals such as dogs, cats, etc. Daily doses of from 5 to 50 mg/kg of animal body weight, preferably about 5 to 25 mg/kg of animal body weight can be administered in single or divided doses.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The following examples further illustrate the preparation of the compounds of this invention.

EXAMPLE 1

3a,7a-trans-5,6-trans-1-[3-[[3-(p-(Acetylphenoxy)-propyl]-methylamino]propyl]hexahydro-3a,5,6,7a-indantetrol, tetraacetate ester A solution of 40 g of 1-[3-(methylamino)propyl]indene in 200 ml of absolute ether is added to 2.5 liters of liquid ammonia at −33°C. Lithium ribbon (35 g) is added over 1.5 hours. The bronze mixture is stirred for 1 hour, and treated with absolute ethanol over 2 hours until the blue color is discharged. The ammonia is evaporated overnight, whereupon water and ether are added with cooling in an ice bath. The layers are separated, the aqueous layer reextracted, and the organic layers are dried (potassium carbonate) and evaporated to give 40 g of 4,7-dihydro-1-[3-(methylamino)propyl]indan as an oil. The crude diene is taken up in 400 ml of toluene and treated with 24 g of phenoxypropylbromide in 100 ml of toluene. The mixture is refluxed for 18 hours, cooled, diluted with ether, and washed several times with water. The organic layers are then shaken with excess 10% hydrochloric acid. The bottom colorless aqueous phase of the 3-phase mixture is drawn off, the toluene-ether layer is decanted, and the isolated middle layer washed with distilled water. The oily hydrochloride is then shaken with excess 10% sodium hydroxide and ether and the organic phase is separated and dried (potassium carbonate). Evaporation gives 25 g of N-methyl-N-phenoxypropylaminopropyl-4,7-dihydroindan.

A solution of 25 g of phenoxypropyl diene in 500 ml of 98% formic acid is treated at 5°C over 10 minutes with 35 ml of 30% hydrogen peroxide. The reaction temperature is kept below 38°C with occasional cooling, and the mixture is allowed to stand overnight at room temperature. Water (500 ml) is added and the mixture is evaporated in vacuo. This process is repeated and the mixture taken down to an oil. This residue is taken up in 300 ml of water and 50 ml of 95% ethanol and made alkaline with 200 ml of 10% sodium hydroxide. The mixture is heated on a steam cone for 1.5 hours, cooled, and extracted with 1.5 liters of ethyl acetate. The combined organic layers are dried (magnesium sulfate), filtered, and evaporated. Benzene is added and the mixture is boiled to remove water azeotropically. The clear solution is concentrated to 150 ml and added to a 500 g dry basic alumina column (Activity IV). Elution with 2 liters of 2.5% methanol in chloroform yields 14 g of 3a,7a-trans-5,6-transhexahydro-1-[3-[methyl(3-phenoxypropyl)amino]propyl]-3a,5,6,7a-indantetrol as a thick oil.

A 6 g fraction of tetrol in 150 ml of acetic anhydride at −78°C is treated with 3.5 ml of 70% perchloric acid. After 18 hours at −20°C, the mixture is cooled in ice-acetone and treated with 100 ml of anhydrous methanol over 1 hour. The mixture is poured into a stirred ice-cooled mixture of ether and concentrated aqueous ammonia. The organic phase is separated, the aqueous phase extracted again with ether, and the organic layers are chromatographed on 200 g neutral alumina (Activity II) in hexane containing 5% ethyl acetate, with increasing amounts of methylene chloride to give 1.2 g of an oil with 95% methylene chloride and 5% ethyl acetate. Elution with 100% ethyl acetate gives 4 g of an oil which crystallizes from ether-hexane to give 2.8 g of pure 3a,7a-trans-5,6-trans-1-[3-[[3-(p-acetylphenoxy)propyl]methylamino]propyl]-hexahydro-3a,5,6,7a-indantetrol, tetraacetate ester.

Recrystallization from ether-hexane gives a 1.7 g analytical sample, melting point 99°–101°C.

EXAMPLE 2

3a,7a-trans-5,6-trans-1-[3-[[2-(o-Ethoxyphenoxy)ethyl]methylamino]-propyl]hexahydro-3a,5,6,7a-indantetrol, tetraacetate ester 3a,7a-trans-5,6-trans-Hexahydro-1-[3-(methylamino)propyl]-3a,5,6,7a-indantetrol, tetraacetate ester (10.0 g), triethylamine (3.0 g) and o-ethoxyphenoxyethyl bromide (6.1 g) are dissolved in 100 ml benzene and heated under reflux for 4 hours. After cooling, the solid is removed by filtration. The filtrate is washed twice with water, dried and the solvent is removed in vacuo leaving 11.8 g of crude oil. Most of this material is dissolved in ether—a small amount of solid is removed by filtration. The ether solution is made acidic using a solution of hydrogen chloride in isopropyl alcohol. The gummy hydrochloride is washed several times with ether. The hydrochloride is then dissolved in water. The solution is made alkaline using 5% potassium carbonate solution and the free base is extracted into ether. The ether solution is dried and the solvent is removed in vacuo leaving 5.6 g of viscous material which crystallizes on standing. This is recrystallized from ether-hexane to give 5.0 g of the title compound, melting point 78°–84° C.

EXAMPLE 3

3a,7a-trans-5,6-trans-1-[3-[[2-(p-Acetylphenoxy)ethyl]methylamino]propyl]hexahydro-3a,5,6,7a-indantetrol, tetraacetate ester A mixture of 4,7-dihydro-1-[3-(methylamino)propyl]indan (15 g, prepared as described in Example 1) and 10 ml of triethylamine in 300 ml of toluene at 0°C is treated dropwise with a solution of 15 g of phenoxyacetyl chloride in 100 ml of toluene. The mixture is stirred and allowed to come to room temperature overnight, then diluted with ether and filtered. The filtrate is washed with 10% hydrochloric acid, then with 10% sodium hydroxide, dried (magnesium sulfate) and evaporated to give 22 g of an oil. This is taken up in 100 ml of dry ether and added to a stirred slurry of 5 g of lithium aluminum hydride in 400 ml of ether under nitrogen. The mixture is refluxed for 3 hours, cooled, and decomposed with saturated sodium carbonate. The white salts are filtered and washed with ether, and the filtrate is evaporated to give 17 g of N-methyl-N-phenoxyethylaminopropyl-4,7-dihydroindan.

The phenoxypropyl diene (17 g) in 300 ml of 98% formic acid is treated over ½ hour at 35°–40°C with 35 ml of 30% hydrogen peroxide. The mixture is allowed to stand at room temperature of 2½ days, water added (same volume), and evaporated in vacuo at a temperature less than 35°C. More water is added and the mixture is evaporated, then taken up in 95% ethanol (300 ml) and treated with 200 ml of 10% sodium hydroxide. After heating for 1 hour on a steam bath, the mixture is cooled and extracted with ether. The extracts are dried (magnesium sulfate), evaporated, dried azeotropically with benzene and evaporated. Chromatography of 600 g of basic alumina (Activity IV) in chloroform followed by 1% methanol in chloroform gives 6 g of crude tetrol which affords 2.8 g of solid tetrol on standing in ether.

The tetrol (2.8 g) in 100 ml of acetic anhydride is cooled to −78°C and treated with 2 ml of 70% perchloric acid and allowed to warm to −20°C overnight. The mixture is then treated at −15°C with 60 ml of methanol over ¾ hour, poured into cooled ether and concentrated ammonium hydroxide. The ether is dried (magnesium sulfate) and evaporated to give an oil. The oil is taken up in ether, and hexane is added, precipitating an oil. When the supernatant shows a single spot on thin layer chromatography, it is filtered and allowed to stand, depositing 1.9 g of the analytical sample of 3a,7a-trans-5,6-trans-1-[3-[[2-(p-acetylphenoxy)ethyl]methylamino]propyl]hexahydro-3a,5,6,7a-indantetrol, tetraacetate ester, melting point 77°–81°C.

EXAMPLE 4

3a,7a-trans-5,6-Hexahydro-1-[3-[methyl(3-phenoxypropyl)-amino]propyl]-3a,5,6,7a-indantetrol, tetraacetate ester 3a,7a-trans-5,6-trans-Hexahydro-1-[3-methylamino)propyl]-3a,5,6,7a-indantetrol, tetraacetate ester (10.0 g) triethylamine (3.0 g) and 3-phenoxypropylbromide (5.2 g) are dissolved in 100 ml benzene and heated under reflux for 5 hours. After cooling the solid is removed by filtration. The filtrate is washed twice with water, dried, filtered and the solvent is removed in vacuo leaving 12.7 g of oil. This material is dissolved in chloroform and extracted twice with dilute hydrochloric acid. Basification of this aqueous extract and extraction yields only a trace of material. The chloroform layer is dried over $MgSO_4$, filtered and taken to dryness in vacuo. The residue is dissolved in water and the aqueous layer is washed twice with ether, then made alkaline and the product is extracted into ether. The ether layer is dried and the solvent is removed in vacuo leaving 5.5 g viscous oil. This is dissolved in ether-hexane and after several weeks in a cold room crystalline material is deposited. This is recrystallized from ether-hexane to give 3.7 g of 3a,7a-trans-5,6-trans-hexahydro-1-[3-[methyl(3-phenoxypropyl)amino]propyl]-3a,5,6,7a-indantetrol, tetraacetate ester, melting point 66°–77°C.

EXAMPLES 5–8

Following the procedure of Example 1, but substituting the compound listed in column I for 1-[3-(methylamino)propyl]indene, the compound listed in column II for phenoxypropylbromide, and the compound listed in column III for acetic anhydride, yields the compound listed in column IV.

| | Column I | Column II | Column III | Column IV |
|---|---|---|---|---|
| 5 | 1-[2-(methylamino)ethyl]indene | phenoxyethylbromide | acetic anhydride | 3a,7a-trans-5,6-trans-1-[2-[[2-(p-acetylphenoxy)ethyl]methylamino]ethyl]hexahydro-3a,5,6,7a-indantetrol, tetraacetate ester |
| 6 | 1-[4-(methylamino)butyl]indene | phenoxybutylbromide | acetic anhydride | 3a,7a-trans-5,6-trans-1-[4-[[4-(p-acetylphenoxy)butyl]methylamino]butyl]hexahydro-3a,5,6,7a-indantetrol, tetraacetate ester |
| 7 | 1-[(methylamino)methyl]indene | phenoxypropylbromide | acetic anhydride | 3a,7a,-trans-5,6-trans-1-[[3-(p-acetylphenoxy)propyl]methylamino]methyl]hexahydro-3a,5,6,7a-indantetrol, tetraacetate ester |
| 8 | 1-[3-(isopropylamino)propyl]indene | phenoxypropylbromide | caproic anhydride | 3a,7a-trans-5,6-trans-1-[3-[[3-(p-caproylphenoxy)propyl]isopropylamino]propyl]hexahydro-3a,5,6,7a-indantetrol, tetracaproate ester |

EXAMPLES 9–12

Following the procedure of Example 2, but substituting the compound listed in column I for 3a,7a-trans-5,6-transhexahydro-1-[3-(methylamino)propyl]-3a,5,6,7a-indantetrol, tetraacetate ester and the compound listed in column II for o-ethoxyphenoxyethyl bromide, yields the compound listed in column III.

| | Column I | Column II | Column III |
|---|---|---|---|
| 9 | 3a,7a-trans-5,6-trans-hexahydro-1-[2-(methylamino)ethyl]-3a,5,6,7a-indantetrol, tetraacetate ester | m-methylphenoxyethyl bromide | 3a,7a-trans-5,6-trans-1-[2-[[2-(m-methylphenoxy)ethyl]methylamino]ethyl]hexahydro-3a,5,6,7a-indantetrol, tetraacetate ester |
| 10 | 3a,7a-trans-5,6-trans-hexahydro-1-[4-(methylamino)butyl]-3a,5,6,7a-indantetrol, tetraacetate ester | p-chlorophenoxyethyl bromide | 3a,7a-trans-5,6-trans-1-[4-[[2-(p-chlorophenoxy)ethyl]methylamino]butyl]hexahydro-3a,5,6,7a-indantetrol, tetraacetate ester |
| 11 | 2,3-trans-4a,8a-trans-decahydro-5-[2-(methylamino)ethyl]-2,3,4a,8a-naphthalenetetrol, tetraacetate ester | phenoxyethyl bromide | 2,3-trans-4a,8a-trans-5-[2-[[2-(phenoxy)ethyl]methylamino]ethyl]decahydro-2,3,4a,4a-naphthalenetetrol, tetraacetate ester |
| 12 | 2,3-trans-4a,9a-trans-hexahydro-7-[2-(methylamino)ethyl]-2,3,4a,9a-benzocycloheptane, tetraacetate ester | phenoxyethyl bromide | 2,3-trans-4a,9a-trans-7-[2-[[2-(phenoxy)ethyl]methylamino]ethyl]hexahydro-2,3,4a,9a-benzocycloheptanetetrol, tetraacetate ester |

What is claimed is:

1. A compound having the structure

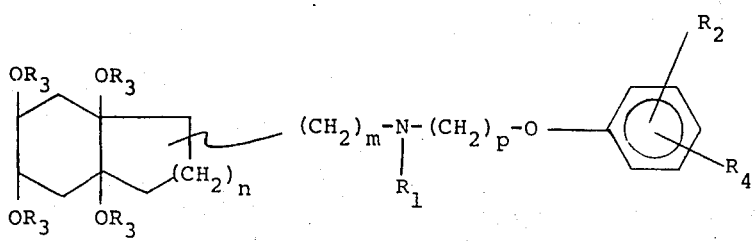

or a pharmaceutically acceptable salt thereof, wherein $R_1$ is alkyl, phenylalkyl or phenylalkyl wherein the ring is substituted by 1 or 2 groups selected from the group of halogen, alkyl or alkoxy having 1–6 carbon atoms, said alkyl moieties having 1–6 carbon atoms; $R_2$ is hydrogen, halogen, alkyl, or alkoxy; $R_3$ is alkanoyl having 1–7 carbon atoms; $R_4$ is hydrogen or alkanoyl having 1–7 carbon atoms; $n$ is 1, 2 or 3; $m$ is 1, 2, 3 or 4; and $p$ is 2, 3 or 4; with the proviso that when $R_4$ is alkanoyl, $R_3$ and $R_4$ are the same.

2. A compound in accordance with claim 1 wherein $n$ is 1.

3. A compound in accordance with claim 1 wherein $n$ is 2.

4. A compound in accordance with claim 1 wherein $n$ is 3.

5. A compound in accordance with claim 2 wherein $R_1$ is alkyl.

6. A compound in accordance with claim 2 wherein $R_1$ is methyl.

7. A compound in accordance with claim 2 wherein $R_3$ is acetyl.

8. A compound in accordance with claim 2 wherein $R_4$ is hydrogen.

9. A compound in accordance with claim 2 wherein $R_4$ is alkanoyl.

10. A compound in accordance with claim 2 wherein $R_1$ is methyl, and $R_3$ is acetyl.

11. A compound in accordance with claim 10 wherein m and p are the same or different and are 2 or 3.

12. The compound in accordance with claim 2 having the name 3a, 7a-trans-5,6-trans-1-[3-[[3-(p-acetylphenoxy)propyl]-methylamino]propyl]hexahydro-3a,5,6,7a-indantetrol, tetraacetate ester.

13. The compound in accordance with claim 2 having the name 3a,7a-trans-5,6-trans-1-[3-[[2-(o-ethoxyphenoxy)ethyl]-methylamino]propyl]hexahydro-3a,5,6,7a-indantetrol, tetraacetate ester.

14. The compound in accordance with claim 2 having the name 3a,7a-trans-5,6-trans-1-[3-[[2-(p-acetylphenoxy)ethyl]-methylamino]propyl]hexahydro-3a,5,6,7a-indantetrol, tetraacetate ester.

15. The compound in accordance with claim 2 having the name, 3a,7a-trans-5,6-trans-hexahydro-1-[3-[methyl(3-phenoxypropyl)amino]propyl]-3a,5,6,7a-indantetrol, tetraacetate ester.

16. A compound having the structure

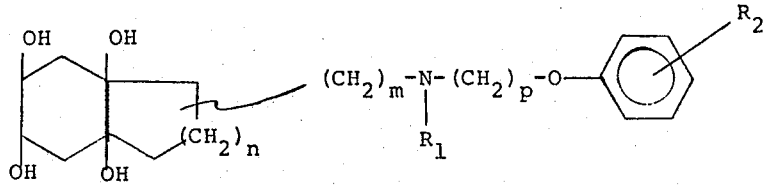

wherein $R_1$ is alkyl, phenylalkyl or phenylalkyl wherein the ring is substitued by 1 or 2 groups selected from the group of halogen, alkyl or alkoxy having 1–6 carbon atoms, said alkyl moieties having 1–6 carbon atoms; $R_2$ is hydrogen, halogen, alkyl, alkoxy or alkanoyl having 1–7 carbon atoms; $n$ is 1, 2 or 3; $m$ is 1, 2, 3 or 4; and $p$ is 2, 3 or 4.

17. A compound in accordance with claim 16 wherein $n$ is 1.

* * * * *